United States Patent [19]

Subramanian et al.

[11] Patent Number: 5,463,030
[45] Date of Patent: Oct. 31, 1995

[54] METAL CHELATING AGENTS FOR MEDICAL APPLICATION

[75] Inventors: Gopal Subramanian, Manlius; Richard F. Schneider, Syracuse, both of N.Y.

[73] Assignee: Research Foundation of the State of New York, Albany, N.Y.

[21] Appl. No.: 251,633

[22] Filed: May 31, 1994

Related U.S. Application Data

[63] Continuation of Ser. No. 695,207, May 3, 1991, abandoned.
[51] Int. Cl.$^6$ .............................. C07F 5/00; A61K 49/00; A61K 51/04
[52] U.S. Cl. ............................................ 534/16; 424/9.365
[58] Field of Search ................................. 534/10, 14, 15, 534/16; 424/1.65

[56] References Cited

U.S. PATENT DOCUMENTS

| | | | |
|---|---|---|---|
| 3,859,337 | 1/1975 | Herz et al. | |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,746,507 | 5/1988 | Quag | 424/9 |
| 4,826,673 | 5/1989 | Dean et al. | 424/9 |
| 4,859,451 | 8/1989 | Quay et al. | 424/9 |
| 4,885,363 | 12/1989 | Tweedle et al. | 540/465 |
| 4,935,518 | 6/1990 | Rocklage et al. | 546/6 |
| 4,957,939 | 9/1990 | Gries et al. | 514/492 |
| 4,963,344 | 10/1990 | Gries et al. | 424/9 |
| 5,011,925 | 4/1991 | Rajagopalan et al. | 544/58.1 |
| 5,077,037 | 12/1991 | Wallace | 424/9 |
| 5,130,120 | 7/1992 | Weber | 424/9 |
| 5,138,040 | 11/1992 | Moore et al. | 534/16 |

FOREIGN PATENT DOCUMENTS

413405  2/1991  European Pat. Off. .

OTHER PUBLICATIONS

Derwent abstract AN 91–052707 of EP 413405, 1991.
Krishnamurthy et al., "Technetium–99m–Iminodiacetic Acid Organic Anions: Review of Biokinetics and Clinical Application in Hepatology", Hepatology, vol. 9, pp. 139–153, 1989.

Bydder et al., "Clinical Use of Contrast Media in Magnetic Resonance Imaging", British Journal of Hospital Medicine, vol. 43, pp. 149–152, 1990.

Vittadini et al., "B–19036, A Potential New Hepatobiliary Contrast for MP Proton Imaging", Investigative Radiology 1988; 23 (Supp 1) S246–S248.

Shtern et al., "MR. Imaging of Blood–borne Liver Matastases in Mice: Contrast Enhancement with Fe–EHPG", Radiology 1991; 178:83–89.

Engelstad et al., "Hepatobiliary Magnetic Resonance Contrast Agents Assessed by Gadolinium–153 Scintigraply", Radiology 1987; 22:232–238.

Elizondo et al., "Preclinical Evaluation of MnDPDP: New Paramagnetic Hepatobiliary Contrast Agent for MR Imaging", Radiology 1991; 178:83–78.

Pavone et al., "Comparison of Gd–BOPTA with GD–DTPA in MR Imaging of Rat Liver" Radiology 1990; 176:61–64.

Saeed et al., "Occlusive and Reperfused Myocardial Infarcts: Differentiation with MnDPDP – enhanced MR Imaging", Radiology 1989; 172:59–64.

Primary Examiner—Gary L. Geist
Assistant Examiner—Lara E. Chapman
Attorney, Agent, or Firm—Morgan & Finnegan

[57] ABSTRACT

The present invention relates to a new group of compounds (e.g., N,N"-bis(2,6-dimethylcarbaniloylmethylene diethylene triamino triacetic acid, N,N'''-bis(pyridoxylamine)diethylene triamino triacetic acid) which can be used as metal chelating agents and can be complexed with paramagnetic metal atoms form new complexes with improved and unexpected stability which make them extremely useful as contrast agents in magnetic resonance imaging and other types of diagnostic imaging. The chelating agents and corresponding paramagnetic metal complexes are derivatives of diethylene triamino pentaacetic acid and triethylene tetraamino hexaacetic acid.

5 Claims, No Drawings

METAL CHELATING AGENTS FOR MEDICAL APPLICATION

This is a continuation of application Ser. No. 07/695,207, filed on May 3, 1991 now abandoned.

BACKGROUND OF INVENTION

Metal-chelating agents have been used as contrast agents and have proven useful in magnetic resonance imaging ("MRI"), radionuclide imaging, ultrasound imaging and X-ray imaging. The overall effect of these contrast agents can be enhanced when the contrast agent is complexed with a metal ion, in particular a paramagnetic metal ion. However, the paramagnetic metal ions used are generally toxic and as a result only low dosages of the contrast agent containing paramagnetic metal ions can be administered. For example, gadolinium exhibits strong paramagnetic properties making it useful as the paramagnetic metal ion portion of the contrast agent complex. However, because any free gadolinium released from a contrast agent will accumulate in the bone marrow, liver and spleen, with resulting toxicity, gadolinium cannot be used to enhance a contrast agent unless it is complexed with a strong chelating agent.

Over the last several years, a number of contrast agents have been proposed for magnetic resonance imaging of the liver. These contrast agents include gadolinium-diethylene triamino pentaacetic acid ("Gd-DTPA") (Venetia et al., "Magnetic Resonance Imaging of the Liver", Top Magnetic Resonance Imaging 1990; 2:1–16); iron ethylene bis (2-hydroxy phenyl glycine) ("Fe-EHPG") (Shtern et al., "MR Imaging of Blood-borne Liver Metastasis in Mice: Contrast Enhancement With Fe-EHPG, Radiology 1991; 178:83–89), gadolinium-hepatic iminodiacetic acid ("Gd-HIDA") (Engelstad et al., "Hepatobiliary Magnetic Resonance Contrast Agents Assessed by Gadolinium-153 Scintigraphy", Invest Radiol. 1987; 22:232–238), gadolinium-benzyloxyproprionyl tetracetate ("Gd-BOPTA") (Pavone et al., "Comparison of Gd-BOPTA with Gd-DTPA in MR Imaging of Rat Liver", Radiology 1990; 176:61–64); and manganese-ethylene dipyridoxal diphosphate ("Mn-DPDP") (Elezondo et al., "Preclinical evaluation of Mn-DPDP: New paramagnetic hepatobiliary contrast agent for MR Imaging", Radiology 1991; 178:83–78).

The liver is known to contain more hepatocytes (78% by volume) than reticuleoendothelial cells (2% by volume) and therefore it is preferable to administer a contrast agent which will initially localize in hepatocytes and which will ultimately be quantitatively excreted in the bile with no resulting long term hepatic or total body retention.

Of the above-mentioned contrast agents, Gd-DTPA has been found not to be suitable for MRI of the liver because of its rapid clearance from the blood and subsequent prompt renal excretion. The other hepatocyte-localizing agents have been found to have low hepatic concentration. For example, the liver concentrates only 37% of the injected dose of Gd-BOPTA, while Mn-DPDP localizes only 47% in the liver. Additionally, up to 6% of manganese is retained in the body after 7 days (Saud et al., "Occlusive and reperfused myocardial infarcts: Differentiation with Mn-DPDP enhanced MR Imaging", Radiology 1989; 172:59–64) Moreover, the Gd-HIDA analysis described in the literature, the gadolinium has been found to be loosely bound to the iminodiacetic acid chelating agent. This minimizes the in vivo stability of the contrast agent during hepatocellular concentration, hepatobiliary excretion and its ultimate elimination from the body.

Nuclear imagers have known for many years that hepatic parenchymal uptake of Tc-99m labeled hepatobiliary agents (HIDA) is greater than that of hepatic metastases. One could reason that MRI of the liver with a new hepatobiliary agent, which has gadolinium substituted for technetium may improve tumor/parenchymal differentiation, given the superior spatial resolution of MRI. However, Gd-HIDA and derivatives thereof, have failed to enhance the image of the gall bladder and have only faintly enhanced images of the liver. Additionally, these compounds have proven unstable in vivo, resulting in the release of gadolinium which is retained in the liver, spleen and bone marrow at excessive and potentially toxic levels.

The present invention relates to a new group of compounds which can be used as metal chelating agents. These compounds when complexed with metal ions, especially paramagnetic metal ions, form new complexes with improved and unexpected stability making them useful as contrast agents in MRI and other types of diagnostic imaging.

An object of this invention is to provide new and improved compounds which can be used as metal chelating agents. A further object of this invention is to provide metal chelating agents which when complexed with metal ions, and in particular paramagnetic metal ions, form new complexes with improved stability. Another object of this invention is to provide metal chelating agents which can be used as an MRI contrast agent which can be administered in lower dosages. Additionally, a further object of this invention is to provide MRI contrast agents and their corresponding metal complexes which can be ionic or nonionic, physiologically tolerable and exhibit a low toxicity. A still further object of this invention is to provide metal chelating agents and their corresponding metal complexes in which the pharmacokinetics, physiological behavior, and biodistribution of these chelating agents and their corresponding metal complexes can be altered. Another object of this invention is to provide a method of synthesizing the chelating agents and their corresponding metal complexes. Moreover, another object of this invention is to provide chemically stable, physiologically tolerable chelating agents which can form complexes with metal ions, and in particular paramagnetic metal ions, and be used in vivo for MRI and other types of diagnostic imaging.

SUMMARY OF INVENTION

These and other objects which will be appreciated by those skilled in the art and are accomplished by compounds with the following formula I:

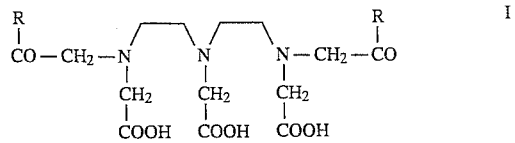

wherein each R is independently an anilino radical, a benzylamino radical, a phenethylamino radical, a pyridoxylamine or pyridoxylamine derivative radical, a para-amino hippuric acid radical and wherein the nitrogen of the above-identified nitrogen-containing radicals are linked to the carbon of the carbonyl group forming the amide linkage.

Moreover, the phenyl ring of the anilino, benzylamino and phenethylamino radicals can be either substituted or unsubstituted. If substituted, the phenyl ring can be substituted with up to five hydroxyls, hydroxyl-containing moieties, alkyl, and/or alkoxy groups.

The chelating agents represented by formula I can then be complexed with various metal ions, especially paramagnetic metal ions, to form stable metal complexes or pharmaceutically acceptable salts thereof.

The resulting complexes localize quantitatively in the hepatocytes in the liver and are quantitatively excreted from the body through the hepatobiliary system and intestines. The pharmacokinetics, biodistribution, lipophilicity, solubility, viscosity, molecular weight and electronic charge of these complexes can be controlled and influenced by the substituent groups on the anilino, benzylamino and phenethylamino radicals groups used. Additionally, the above-identified properties can be controlled and influenced by using a pyridoxylamine or pyridoxylamine derivative radical, or a para-amino hippuric acid radical. The quantity of the metal complex needed to produce the enhanced signal change required for MRI using these new contrast agents is believed to be approximately 1/10 of the dosage required for current agents, such as Gd-DTPA. Therefore, these new complexes should have the added benefit of reduced or minimal toxicity.

Additionally, the objects can be accomplished with compounds and chelating agents having the formulas II and III as follows:

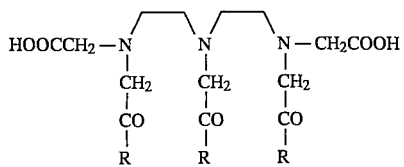

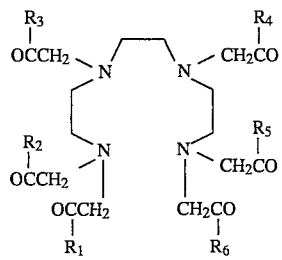

wherein in Formula II, each R' is independently an unsubstituted or substituted anilino radical, benzylamino radical, phenethylamino radical, a pyridoxylamine or pyridoxylamine derivative radical, or derivative thereof, or a para-amino hippuric acid radical.

In formula III, the $R_1$, $R_2$, $R_3$, $R_4$, $R_5$ and $R_6$ groups are an a hydroxyl radical, an anilino radical, a benzylamino radical, a phenethylamino radical, a pyridoxylamine or pyridoxylamine derivative radical, or a para-amino hippuric acid radical with the proviso that at least 2 of the $R_1$, $R_2$, $R_3$, $R_4$, $R_5$ and $R_6$ groups, and not more than 4 of the $R_1$, $R_2$, $R_3$, $R_4$, $R_5$ and $R_6$ groups are a hydroxy radical. In the case of the above-identified nitrogen-containing radicals, the nitrogen is linked to the carbon of the carbonyl group forming the amide linkage.

The phenyl ring of the anilino, benzylamino and phenethylamino radicals can be either substituted or unsubstituted. If substituted, the phenyl ring can be independently substituted with up to five hydroxyl, hydroxyl-containing moieties, alkyl, and/or alkoxy groups.

Because of the structural similarity between compounds represented by formulas I, II and III, it is expected that when the compounds represented by formulas II and III are complexed with metal ions, especially paramagnetic metal ions, these complexes will have charactersitics similar to those exhibited by the compounds and corresponding complexes represented by Formula I. It is also expected that the complexes represented by formulas II and III will also localize quantitatively in the hepatocytes of the liver and will also be quantitatively be excreted from the body. It is further believed that the pharmacokinetics and biodistribution of the compounds represented by formulas II and III may also be varied to produce beneficial and improved effects similar to those obtained by the compounds and corresponding complexes of formula I.

While the chelating agents represented by general formulas I, II and III have been described in terms of their ability to be complexed with metal ions, and preferably with paramagnetic metal ions, for ultimate use as MRI contrast agents, those skilled in the art will appreciate that the chelating agents represented by formulas I, II and III may also be complexed with other divalent or trivalent cations so that the resulting complexes can be used for other types of diagnostic imaging such as x-ray, radionuclide and ultrasound.

DETAILED DESCRIPTION

The chelating agents contemplated by this invention are derivatives of diethylenetriamine pentaacetic acid ("DTPA")

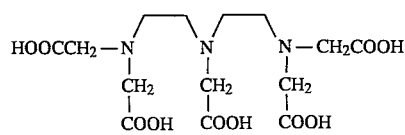

The chelating agents and corresponding metal complexes of this invention are represented by formula I

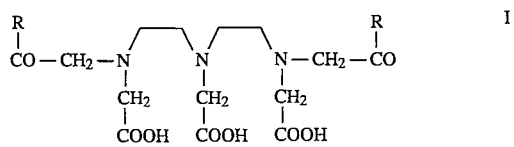

wherein in R is independently an anilino radical, a benzylamino radical, a phenethylamino radical, a pyridoxylamine or pyridoxylamine derivative radical, or a para-hippuric acid radical. The nitrogen-containing radicals represented by R are linked to the carbon of the carbonyl group forming the amide linkage.

The phenyl groups of the anilino radical, benzylamino radical or phenethylamino radical can be substituted with up to five substituents. Among the groups which can be substituted onto the phenyl ring are various hydroxyl, hydroxyl-containing moieties, lower alkyl ($C_1$–$C_6$), or lower alkoxy ($C_1$–$C_6$) groups. The most preferred substituents are alkyl groups. The alkyl and alkoxy groups may be optionally further substituted by hydroxyl or amino groups.

Among the preferred lower alkyl groups contemplated by this invention are methyl, ethyl, isopropyl, n-propyl and n-butyl, the most preferred being methyl. The most preferred positions on the phenyl ring for the substitution of the alkyl groups to occur are the 2- and 6-positions.

Among the preferred hydroxyl-containing moieties which can be substituted onto the phenyl ring of the anilino, benzylamino or phenethylamino radicals are amino propanediol or erythritol, the most preferred being amino propanediol. The most preferred position on the phenyl ring for the substitution with hydroxyl groups or hydroxyl-containing groups to occur is the 4-position.

Among the lower alkoxy groups which can be used are methoxy, ethoxy and butoxy, the most preferred being butoxy. The most preferrable position on the phenyl ring for substitution with the alkoxy groups to occur is the 4-position.

The pyridoxylamine or pyridoxylamine derivative radicals contemplated by this invention include pyridoxylamine and pyridoxylamine 5 phosphate, the most preferred being the pyridoxylamine 5 phosphate.

It is also expected by the inventors, because of the similarity of structures, other derivatives of DTPA and derivatives of triethylene tetraamino hexaacetic acid ("TTHA") will provide benefits similar to those achieved by the previously described derivatives of DTPA.

The other derivatives of DTPA which are contemplated by this invention are represented by the general formula

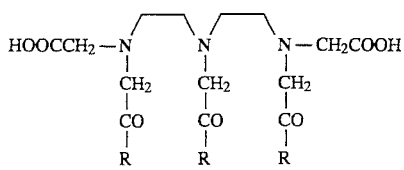

II wherein in R is independently an anilino radical, a benzylamino radical, a phenethylamino radical, a pyridoxylamine or pyridoxylamine derivative radical, or a para-amino hippuric acid radical. The nitrogen of the nitrogen-containing radicals represented by R are linked to the carbon of the carbonyl group forming an amide linkage.

TTHA is represented by the formula

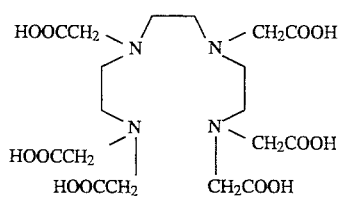

The derivatives of TTHA which are contemplated by this invention are represented by the formula

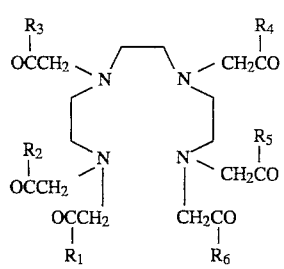

III wherein the $R_1$, $R_2$, $R_3$, $R_4$, $R_5$ and $R_6$ groups are a hydroxyl radical, an anilino radical, a benzylamino radical, a phenethylamino radical, a pyridoxylamine or pyridoxylamine derivative radical, or a para-amino hippuric acid radical with the proviso that at least 2 of the $R_1$, $R_2$, $R_3$, $R_4$, $R_5$ and $R_6$ groups, and not more than 4 of the $R_1$, $R_2$, $R_3$, $R_4$, $R_5$ and $R_6$ groups are a hydroxy radical. In particular, in formula III, $R_1$ and $R_6$ are R when $R_2$, $R_3$, $R_4$ and $R_5$ are OH, or $R_3$ and $R_4$ are hydroxyl radicals when $R_1$, $R_2$, $R_5$ and $R_6$ are R as in formula I, or $R_2$ and $R_5$ are hydroxyl radicals when $R_1$, $R_3$, $R_4$ and $R_6$ are R and wherein R is an anilino radical, a benzylamino radical, a phenethylamino radical, a pyridoxylamine or pyridoxylamine derivative radical, or a para-amino hippuric acid radical.

In both the compounds represented by formulas II and III, the phenyl groups of the anilino, benzylamino or phenethylamino radicals can be substituted independently with up to five substituents. Among the groups that can be substituted onto the phenyl ring are various hydroxyl, hydroxyl-containing moieties, lower alkyl ($C_1$–$C_6$) or lower alkoxy ($C_1$–$C_6$). The alkyl and/or alkoxy radicals can optionally be further substituted by hydroxyl or amino groups. The most preferred substituents are the alkyl groups.

Among the preferred lower alkyl groups contemplated by this invention are methyl, ethyl, isopropyl, n-propyl and n-butyl, the most preferred being methyl. The most preferred positions on the aromatic ring for substitution with the alkyl groups are the 2- and 6-positions.

Among the preferred hydroxyl-containing moieties which can be substituted onto the phenyl ring of the anilino, benzylamino and phenethylamino radicals are amino propanediol or erythritol, the most preferred being amino propanediol. The most preferred position on the aromatic ring for the substitution of the hydroxyl or hydroxyl-containing moieties groups to occur is the 4-position.

Among the lower alkoxy groups which can be used are methoxy, ethoxy and butoxy, the most preferred being butoxy. The most preferred position on the aromatic ring for substitution with the alkoxy groups is the 4-position.

Moreover, pyridoxylamine or pyridoxylamine derivative radicals contemplated by this invention include pyridoxylamine and pyridoxylamine 5 phosphate, the most preferred being pyridoxylamino 5 phosphate.

The DTPA derivatives represented by formula I can be produced by reacting cyclic DTPA dianhydride with two molar equivalents of a primary amine containing moiety (e.g., anilines, pyridoxylamine, etc.) in a suitable solvent such a pyridine at a temperature of about 110°–120° C. for about 1–3 hours. The desired DTPA derivative can then be precipitated from solution by cooling.

The DTPA derivatives represented by formula II can be produced by reacting diethylene triamine ("DTA") with a halogenated acetic acid to form diacetic acid (substituted) DTA containing three amino groups. This compound is then conjugated with three molar equivalents of halogenated acetanilide or any primary amine treated with alpha chloro acetyl chloride to form a tri substituted DTPA.

The TTHA derivatives represented by formula III can be obtained when triethylene tetraamine is reacted with 2 molar equivalents of a halogenated acetanilide at a pH greater than about 10. The mixture is refluxed in ethanol for about 1–6 hours. The resulting di-substituted amine is then reacted with 4 molar equivalents of a halogenated acetic acid at a pH greater than about 10 for about 3–4 hours. The resulting substituted TTHA is then recovered.

The new metal chelating agents contemplated by this invention can be complexed with metal ions, especially paramagnetic metal ions, to form stable complexes. Among the metals which can be used are those from the lanthanide series (e.g., elements of atomic numbers 57–71, such as gadolinium, samarium, and europium), iron, indium, gallium, technetium, chromium and manganese. The preferred metals are gadolinium, europium, iron, manganese and technetium. Gadolinium is the most preferred because it is highly paramagnetic. Additionally, the metal chelating agents of this invention may be complexed with other divalent or trivalent cations if contrast agents for use in other types of diagnostic imaging such as x-ray imaging, radionuclide imaging or ultrasound imaging are desired.

Methods used to complex the chelating agents with metal ions are well known in the art. For example the chelating agent can be dissolved in water or another solvent to which is added the salt, oxide or hydroxide of the desired metal. The pH of the resulting solution is adjusted typically with sodium hydroxide and the mixture is heated. The resulting complex can then be separated from the solution using known procedures (e.g., passing through an ion exchange column).

The complex may then be sterilized so that it can be administered to mammals. See, for example, the procedure disclosed in U.S. Pat. No. 4,859,451 issued to Quay et al., (column 3, line 59 through column 4, line 43) the entire disclosure of which is incorporated herein by reference.

EXAMPLE 1

N,N"-bis (2,6-dimethylcarbaniloylmethylene) diethylenetriamine triacetic acid

DTPA (78.6 g.) was heated to about 70° C. with a mixture of acetic anhydride (75.6 ml) and anhydrous pyridine (102.2 ml) for 18 hours and 65.9 g. of diethylenetriamine pentaacetic acid dianhydride ("DTPADA") was obtained. DTPADA (64.3 g.) was then heated with an excess of 2,6-dimethylaniline (50.2 g) in anhydrous pryridine (1200 ml) and refluxed at a temperature of about 115° C. for 2 hours. The reaction mixture was then cooled and added to 1500 ml of ethyl acetate. The resulting mixture was chilled for about 16 hours to a temperature of about 4° C. The precipitate was collected, washed with ethyl acetate and dried under vacuum at 97° C. and 0.5 mm for about 16 hours. About 59.8 g of N,N"-bis (2,6-dimethylcarbaniloylmethylene) diethylenetriamine triacetic acid ("DTPA-bis 2,6-dimethylaniline") was obtained as the monohydrate. The melting point was determined to be 195°–199° C. and elemental analysis determined for $C_{30}H_{43}N_5O_9$ was 58.4% C, 6.76% H, and 11.22% N.

DTPA-bis (2,6-dimethylaniline) is represented by the following formula:

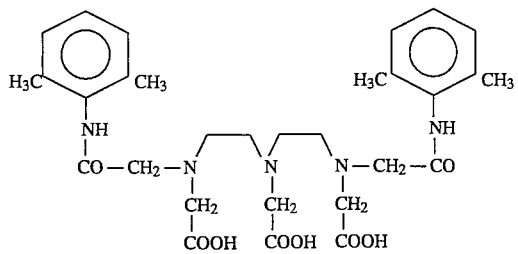

EXAMPLE 2

Gadolinium III chelate of DTPA-bis (2,6-dimethylaniline)

10 g of DTPA-bis (2,6-dimethylaniline) synthesized in Example 1 was mixed with 4.62 ml of sodium hydroxide (1.08N) in a 20 ml serum vial equipped with a magnetic stirrer. The mixture was stirred at room temperature for about 5 minutes until most of the solid had dissolved. 4.76 ml of gadolinium chloride (0.333N) was added and the mixture was placed in a 90° C. oil bath and stirred for about 160 minutes. The mixture was then cooled and a mixed bed ion exchange resin (AG-501-XS) was added and stirred for about 15 minutes. The pH was measured and found to be 2.40. This resin was removed by filtration and washed three times with distilled water. The pH of the combined filtrate and water washes was raised to 7.25 with sodium hydroxide (about 3 drops of NaOH). The resulting solution was filtered and evaporated to dryness. Anhydrous ethanol (50 ml) was added to dissolve the residue and the mixture was again evaporated to dryness to yield 1.08 g (90% yield) of Gd (III) chelate of DTPA-bis (2,6-dimethylaniline).

EXAMPLE 3

To demonstrate that Gd-DTPA-bis (2,6-dimethylaniline) undergoes improved hepatic uptake, biliary excretion and ultimate elimination from the body, radioactive Gd-153 was complexed with DTPA-bis (2,6-dimethylaniline) as follows.

DTPA bis (2,6-dimethylaniline) (0.333 g) and 1.54 ml of sodium hydroxide (1.08N) were placed into a 5 ml serum vial. The mixture was stirred at room temperature for five minutes. The solution was placed into a 90° C. oil bath and 0.143 ml of Gd-153.$Cl_3$ was added along with 1.59 ml of $GdCl_3$ (0.333N $GdCl_3$ solution). The vial was stirred in the oil bath for about 160 minutes. The vial was then cooled and about 1.83 g of mixed bed ion exchange resin was added and stirred for about 15 minutes. The mixture was filtered and washed with 1.5 ml of distilled water. The pH of the solution was adjusted to 7–7.5. The final volume (3.9 ml) was placed in a clean syringe and assayed for Gd-153. The activity was found to be 0.267 mCi/ml.

The Gd-153 in dilute hydrochlorine acid was obtained from Dupont-NEN Pharmaceuticals, Boston, Mass. This was mixed with $GdCl_3.6H_2O$. Molar equivalents of Gd-153, labeled $GdCl_3.6H_2O$ and DTPA-bis (2,6-dimethylaniline) were mixed together. The pH of the solution was adjusted to 10.0 and heated to about 90° C. for 3 hours. The pH was then adjusted to 7.0–7.5 with dilute sodium hydroxide. The resulting solution was passed through 3 cm×1 cm mixed (anionic-cationic) bed resin. The neutral radioactive Gd-153 complex was collected and assayed.

Biodistribution in Mice

Groups of four mice were individually injected in the tail vein with 20 μM/Kg of body weight (10–20 μCi) of Gd-153 labeled DTPA-bis (2,6-dimethylaniline). Each group of mice was sacrificed at intervals of 1,3 and 24 hours. The blood was collected from the heart just before the animals were sacrificed and the animals were dissected and individual organs were assayed. The percent dose in each organ are various time are shown in Table I.

TABLE I

| | % DOSAGE | | |
|---|---|---|---|
| | 1 Hour AVERAGE | 3 Hour AVERAGE | 24 Hours AVERAGE |
| Blood | .4441 | .0188 | .0038 |
| Lungs | .0326 | .0075 | .0085 |
| Liver | 22.95 | 2.805 | 1.659 |
| Spleen | .0214 | .0096 | .0042 |
| Right Kidney | .6676 | .5235 | .1102 |
| Left Kidney | .7115 | .4528 | .1050 |

TABLE I-continued

| | % DOSAGE | | |
|---|---|---|---|
| | 1 Hour AVERAGE | 3 Hour AVERAGE | 24 Hours AVERAGE |
| Muscle | .6207 | .6183 | .0861 |
| Bone | .1489 | .0678 | .1551 |
| Stomach | .2113 | .1254 | .0468 |
| Small Intestine | 36.08 | 52.10 | .1533 |
| Large Intestine | .0781 | 1.471 | .5091 |
| Urine | 26.30 | 32.13 | |

Whole Body Retention In Rate

A group of four rates were injected in the tail vein with about 100 μCi of Gd-153 and about 20 μM/Kg body weight of the gadolinium complex. The rats were counted in a scintillation well counter at zero time daily for a period of seven days. The counts obtained at zero time were 100 percent of the dose and every day counts were determined. The results are shown in Table II.

TABLE II

| | % Retained | | | | | |
|---|---|---|---|---|---|---|
| Rat | Day 0 | Day 1 | Day 2 | Day 5 | Day 6 | Day 7 |
| 1 | 100 | 4.1 | 2.8 | 2.2 | 2.1 | 1.8 |
| 2 | 100 | 3.5 | 2.4 | 2.0 | 1.7 | — |
| 3 | 100 | 5.7 | 2.0 | 1.7 | 1.7 | 1.4 |
| 4 | 100 | 3.1 | 2.8 | 1.7 | 1.8 | 1.5 |
| AVG. | — | 4.1 | 2.5 | 1.9 | 1.83 | 1.57 |

EXAMPLE 4

N,N''-bis (pyridoxylamidomethylene) diethylenetriamine triacetic acid

DTPA cyclic dianhydride (3.27 g) and anhydrous pyridine (122 ml) were placed into a flask with a motorized stirrer. Pyridoxylamine dihydrochloride monohydride (5.0 g) was added to the flask and the mixture was refluxed for about 52 hours at a temperature of about 115° C. The supernatant was discarded and the residue was dissolved in anhydrous methanol (50 ml). The solution was then filtered. The filtrate was added to about 600 ml of ethyl acetate which was rapidly stirred. The solution was chilled to about 4° C. for about 16 hours. The precipitated bis (pyridoxylamine) diethylenetriamine triacetic acid was collected and dried yielding 6.8 g of crude product. This crude product was extracted with 900 ml of boiling anhydrous ethanol. The mixture was then cooled, treated with carbon, filtered and evaporated to a volume of about 150 ml. The resulting solution was chilled and maintained at about −30° C. for 24 hours and 1.9 g of DTPA-bis pyridoxylamine was recovered (29.9% yield).

EXAMPLE 5

Gadolinium III chelate of DTPA-bis pyridoxylamide.

0.50 g of the DTPA-bis pyridoxylamine synthesized in Example 4 was reacted with 0.15 g of Gd(OH)$_3$ and 3.6 ml of water. The pH of the mixture was adjusted to 7.51 with sodium hydroxide. The mixture was then heated in an oil bath at a temperature of about 90° C. for about 45 minutes. The mixture was cooled and the pH adjusted to 7.08 with sodium hydroxide. 5.0 ml of the product was recovered. The concentration of the resulting Gd-DTPA bis pyridoxylamine was determined to be 0.144 moles/liter with an osmotic pressure of 646 m Os moles/liter.

EXAMPLE 6

N,N''-bis (2,4,6-trimethylcarbaniloylmethylene)diethylenetriamine triacetic acid DTPA dianhydride (8.04 g) and anhydrous pyridine (300 ml) were placed into a 1000 ml three-necked flask equipped with a motorized stirrer, moisture protected reflux condenser and heating mantle. The mixture was stirred five minutes at room temperature. 2,4,6-trimethylaniline (6.08 g) was added in one lot and the reaction mixture refluxed gently for 2 hours at a temperature of about 115° C. The cooled reaction mixture was poured into 1500 ml ethyl acetate and chilled 16 hours at 4° C. The precipitated bis amide was collected and washed with ethyl acetate and dried under vacuum (97° C., 0.5 mm) for 16 hours to yield N,N''-bis(2,4,6-trimethylcarbaniloylmethylene) diethylenetriamine triacetic acid. 7.3 g of the product was recovered for a yield of 51.7%. Elemental analysis determined for $C_{23}H_{45}N_5O_8$ was 61.22% C, 7.13% H and 11.16% N.

EXAMPLE 7

N,N''-bis(2,6-diethylcarbaniloylmethylene) diethylenetriamine triacetic acid

DTPA dianhydride (8.04 g) and anhydrous pyridine (300 ml) were placed into a 1000 ml three-necked flask equipped with a motorized stirrer, moisture protected reflux condenser and heating mantle. The mixture was stirred five minutes at room temperature. 2,6-diethylaniline (6.72 g) was added in one lot and the reaction mixture refluxed gently for 2 hours at a temperature of about 115° C. The cooled reaction mixture was poured into 1500 ml ethyl acetate and chilled 16 hours at 4° C. The precipitated bis amide was collected and washed with ethyl acetate and dried under vacuum (97° C., 0.5 mm) for 16 hours to yield N,N''-bis(2,6-diethylcarbaniloylmethylene) diethylenetriamine triacetic acid. 9.4 g of the product was recovered for a yield of 63.5%. Elemental analysis determined for $C_{34}H_{49}N_5O_8$ was 62.27% C, 7.53% H and 10.68% N.

EXAMPLE 8

N,N''-bis (4-butylcarbaniloylmethylene)diethylenetriamine triacetic acid

DTPA dianhydride (8.04 g) and anhydrous pyridine (300 ml) were placed into a 1000 ml three-necked flask equipped with a motorized stirrer, moisture protected reflux condenser and heating mantle. The mixture was stirred five minutes at room temperature. 4-butylaniline (6.72 g) was added in one lot and the reaction mixture refluxed gently for 2 hours at a temperature of about 115° C. The cooled reaction mixture was poured into 1500 ml ethyl acetate and chilled 16 hours at 4° C. The precipitated bis amide was collected and washed with ethyl acetate and dried under vacuum (97° C., 0.5 mm) for 16 hours to yield N,N''-bis(4-butylcarbaniloylmethylene) diethylenetriamine triacetic acid. 4.25 g of the product was recovered for a yield of 28.8%. Elemental analysis determined for $C_{34}H_{49}N_5O_8$ was 62.27% C, 7.53% H and 10.68% N.

EXAMPLE 9

N,N"-bis[4-(carboxymethyleneaminocabonyl) carbaniloylmethylene]diethylenetriamine triacetic acid DTPA dianhydride (8.04 g) and anhydrous pyridine (300 ml) were placed into a 1000 ml three-necked flask equipped with a motorized stirrer, moisture protected reflux condenser and heating mantle. The mixture was stirred five minutes at room temperature. Para-amino hippuric acid (8.74 g) was added and the reaction mixture refluxed gently for 2 hours at a temperature of about 115° C. The cooled reaction mixture was poured into 1500 ml ethyl acetate and chilled 16 hours at 4° C. The precipitated bis amide was collected and washed with ethyl acetate and dried under vacuum (97° C., 0.5 mm) for 16 hours to yield N,N"-bis[ 4-(carboxymethyleneaminocarbonyl)carbaniloylmethylene]diethylenetriamine triacetic acid ("DTPA-bis-(para-amino hippurate)"). 9.1 g of product was recovered for a yield of 54.2%. Elemental analysis determined for $C_{32}H_{39}N_7O_{14}$ was 51.54% C, 5.27% H and 13.15% N.

The resulting product is represented by the following formula:

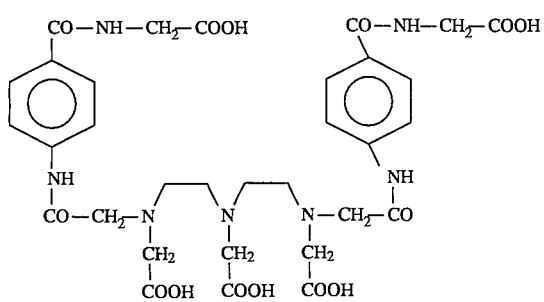

EXAMPLE 10

One mole of N,N'-ethylene diamine diacetic acid is refluxed for 16 hours with 20 moles of 2-bromo acetalydehyde dimethyl acetal in the presence of 2 moles of sodium carbonate and a 1:1 mixture of ethanol and water to yield N,N'-bis(2,2 dimethyoxy)-N,N'-bis(carboxymethyl)ethylene diamine. The resulting product is then refluxed with aqueous hydrochloric acid to produce N,N'-bis (formylmethyl)-N,N'-bis (carboxymethyl) ethylene diamine. One mole of the resulting dialdehyde is then reacted with 2.0 moles of the desired primary amine in the presence of a catalytic amount of p-toulene sulfonic acid in refluxing benzene to yield N,N'-bis (carboxymethyl) ethylene diamine. The N,N'-bis (carboxymethyl) ethylene diamine is hydrogenated in the presence of 10% palladium on charcoal at 50 psi hydrogen and a temperature of 25° C. N,N"-bis (substituted) N,N'-bis (carboxymethyl) triethylene tetramine will be obtained. This compound can then be treated with 2 moles of bromoacetic acid at pH of 11.0 and a temperature of 60° C. for 48 hours to yield the TTHA derivative N,N'''-bis (substituted)-N,N',N'',N'''-tetra carboxy methyl triethylethylene tetraamine.

EXAMPLE 11

To demonstrate the improved nature of contrast agents of this invention two of the DTPA derivatives contemplated by this invention were synthesized. First, DTPA-bis (2,6-dimethylaniline) was prepared following the procedure of Example 1. The second DTPA derivative prepared was DTPA-bis-(para-amino hippurate) following the procedure of Example 9. Para-amino hippuric acid (PAH) is a widely used renal tubular function agent.

Both compounds were labeled with Tc-99m. 40 mg. of both bis amides were dissolved in 5 ml of alkaline water at pH 7.5 and 500 μg of stannous chloride in 0.05M HCl was added to both bis amide solutions. The pH was adjusted to 6.8–7.0. One milliliter of each of the resulting solutions were mixed with 0.5 to 1 ml of Tc-99m pertechnetate (25–40 mCi) and incubated at room temperature for 10 minutes. Samples were analyzed by ITLC SG/saline and paper/acetone to check for colloids and free $TcO_4$. The labeling was greater than 90%. No further purification was performed.

Two albino rabbits weighing 3–4 kg, were injected with 3.5 Mci DTPA bis (2,6 dimethylaniline) and 4.5 Mci of DTPA bis-(para amino hippurate). Anterior images were obtained with a gamma camera fitted with a medium resolution collimator. The neutral DTPA bis (2,6 dimethylaniline) localized in the liver and was excreted by the hepatocytes whereas the anionic DTPA bis-(para amino hippurate) was excreted predominantly through the kidney.

To determine the net charge on the Tc-99m labeled aniline substituted DTPA, paper electrophoresis was performed at 300 volts for 1½ hours using Whatman #1 paper and pH 8.2 barbital buffer. After the run, the electrophoresis strip was cut into 1 cm sections and counted in a scintillation well counter. For comparison purposes, electrophoreses were performed with Tc-99m pertechnetate and Tc-99m DTPA. Most of the radioactivity associated with bis anilide DTPA stayed at the origin. The ITLC quality control tests showed that the Tc-99m compound was water soluble and contained negligible quantity of colloids and free pertechnetate.

These results clearly demonstrate that it is possible to prepare bifunctional chelating agents of bis amides of DTPA and label them with Tc-99m. The bis anilide DTPA - Tc-99m complex had a neutral charge similar to the trivalent metal complexes. This example also demonstrates that it is possible to alter biodistribution of the DTPA derivatives contemplated by this invention by selective substitution of functional groups. These results further demonstrate that one can introduce in vivo specificity by incorporating specific functional groups into these chelating agents without compromising their chelating ability. These results suggest that Tc-99m labeling of TTHA-based chelating agents should be possible and it is believed that similar results as contrast agents can be obtained with TTHA based chelating agents.

Now that the preferred embodiment of the present invention have been described in detail, various modifications and improvements thereon will be readily apparent to those skilled in the art. Accordingly, the spirit and scope of the invention are to be limited by the appended claims, and not by the foregoing specification.

We claim:
1. A complex comprising the following formula

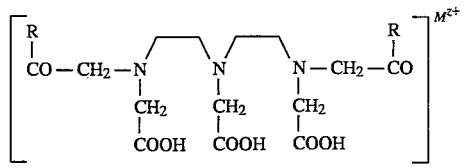

a nitrogen containing radical selected from a para-amino hippuric acid radical, a substituted para-amino hippuric acid radical, a substituted anilino radical, a substituted benzylamino radical or a substituted phenethylamino radical in which the phenyl group of said radicals are independently substituted with amino propanediol or erythritol wherein the nitrogen of the nitrogen containing radicals represented by R is linked to the carbon of the carbonyl group forming an amide linkage and wherein M is a paramagnetic ion selected from the group of elements having atomic numbers of 57–71 and z is a valence of 2+ or 3+.

2. A complex of claim 1 wherein the paramagnetic ion is gadolinium.

3. A complex of claim 1 wherein R is para-amino hippuric acid and the paramagnetic ion is gadolinium.

4. A complex of claim 1 wherein R is 2–6 dipropylanilino, 4 amino propanediol and the paramagnetic ion is gadolinium.

5. A contrast agent useful in magnetic resonance imaging comprising a complex according to claim 1 and a pharmaceutically acceptable salt.

* * * * *